United States Patent [19]

Harrison et al.

[11] Patent Number: 5,684,017
[45] Date of Patent: Nov. 4, 1997

[54] BENZENESULFONYLIMINE DERIVATIVES AS INHIBITORS OF IL-1 ACTION

[75] Inventors: Boyd L. Harrison, Cincinnati, Ohio; George Ku, Burlington, Mass.; Scott B. Meikrantz, Carson City, Nev.; Christopher R. Dalton, Mundelein, Ill.; David M. Stemerick, Fairfield, Ohio

[73] Assignee: Merrell Pharmaceuticals Inc., Cincinnati, Ohio

[21] Appl. No.: 649,663

[22] PCT Filed: Nov. 3, 1994

[86] PCT No.: PCT/US94/12658

§ 371 Date: Aug. 6, 1996

§ 102(e) Date: Aug. 6, 1996

[87] PCT Pub. No.: WO95/14669

PCT Pub. Date: Jun. 1, 1995

Related U.S. Application Data

[63] Continuation of Ser. No. 159,014, Nov. 29, 1993, abandoned.

[51] Int. Cl.$^6$ .................. A61K 31/47; C07D 215/42
[52] U.S. Cl. ........................... 514/313; 546/159
[58] Field of Search ..................... 546/159; 514/313

[56] References Cited

U.S. PATENT DOCUMENTS

| | | |
|---|---|---|
| 3,742,951 | 7/1973 | Zadffaroni . |
| 3,797,494 | 3/1974 | Zadffaroni . |
| 3,921,636 | 11/1975 | Zaddaroni . |
| 3,996,934 | 12/1976 | Zadffaroni . |
| 4,031,894 | 6/1977 | Urquhart et al. . |

FOREIGN PATENT DOCUMENTS 0303387  2/1988  European Pat. Off. .

OTHER PUBLICATIONS

Richard L. Jackson et al, *Current Drugs: Anti–Atherosclerotic Agents,* Oct. 1991, pp. B31–B41.
Ivan G. Otterness et al, *Cytokine,* vol. 3, No. 4, (Jul.) 1991: pp. 277–283.
Kjell Ohlsson et al, *Nature,* vol. 348, Dec. 6, 1990, pp. 550–552.
Masayuki Matsuda et al, *Journal of Neurological Sciences,* 102 (1991) pp. 100–104.
Pierre F. Piguet et al, *Cytokine,* vol. 5, No. 1 (Jan.) 1993: pp. 57–61.
Stellan Sandler et al, *Autoimmunity,* 1991, vol. 10: pp. 241–253.
Nobuyuki Miyasaka et al, *Arthritis and Rheumatism,* vol. 31, No. 4 (Apr. 1988).
Scott K. Drumm et al, *Ann. Rec. Immunol,* 1985: pp. 263–287.
Antonio M. Echavarren et Al., *J. Am. Chem. Soc.,* 1988, 110, pp. 4051–53 with attachment.
Francesco G. Salituro et al., *J. Org. Chem,* 1988, 53, 6138–6139.
Thomas L. Guggenheim, *Tetrahedron Letters,* vol. 25, No. 12, pp. 1253–1254, 1984.

*Primary Examiner*—Patricia L. Morris
*Attorney, Agent, or Firm*—Michael J. Sayles

[57] ABSTRACT

The present invention relates to novel benzenesulfonylimine derivatives and their use as inhibitors of Interleukin-1 (IL-1) action. Such inhibitors are useful in the treatment of various disease states as disclosed herein including: rheumatoid arthritis, multiple sclerosis, diabetes mellitus, atherosclerosis, septic shock and pulmonary fibrosis.

7 Claims, No Drawings

BENZENESULFONYLIMINE DERIVATIVES AS INHIBITORS OF IL-1 ACTION

The present application has an effective international filing date of Nov. 3, 1994 as application PCT/US94/12658 which designated the U.S. and entered U.S. national phase under 35 USC 371 concurrently herewith, which application is a continuation of application Ser. No. 08/159,014 filed on Nov. 29, 1993, now abandoned.

The present invention relates to novel benzenesulfonylimine derivatives and their use as inhibitors of Interleukin-1 (IL-1) action. Such inhibitors are useful in the treatment of various disease states as disclosed herein including: rheumatoid arthritis, multiple sclerosis, diabetes mellitus, atherosclerosis, septic shock and pulmonary fibrosis.

SUMMARY OF THE INVENTION

The present invention provides novel benzenesulfonylimine derivatives of the formula:

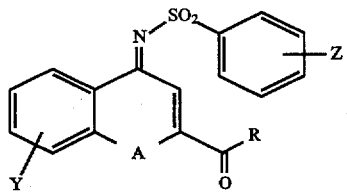

Formula I wherein

A is NH, O, or S;

R is $C_1$–$C_6$ alkyl radical of branched or straight chained or cyclic configuration, phenyl, or substituted phenyl bearing from 1 to 3 substituents chosen independently from the group: hydrogen, $C_1$–$C_4$ alkyl, $C_1$–$C_4$ alkoxy, halogen, —NHC(O)CH$_3$, amino, or hydroxy;

Z is from 1 to 3 substituents independently chosen from the group: hydrogen, $C_1$–$C_4$ alkyl, $C_1$–$C_4$ alkoxy, or halogen;

Y is from 1 to 3 substituents independently chosen from the group: hydrogen, $C_1$–$C_4$ alkyl, $C_1$–$C_4$ alkoxy, halogen.

DETAILED DESCRIPTION OF THE INVENTION

As used in this application:

a) the term "halogen" refers to a fluorine atom, chlorine atom, bromine atom, or iodine atom;

b) the terms "$C_1$–$C_4$ alkyl" refer to a branched or straight chained alkyl radical containing from 1 to 4 carbon atoms, such as methyl, ethyl, n-propyl, isopropyl, n-butyl, isobutyl, t-butyl, etc;

c) the term "$C_1$–$C_6$ alkyl" refer to a cyclic, branched, or straight chained alkyl radical containing from 1 to 6 carbon atoms, such as methyl, ethyl, n-propyl, isopropyl, n-butyl, isobutyl, n-pentyl, cyclopentyl, n-hexyl, cyclohexyl, etc;

d) the terms "$C_1$–$C_4$ alkoxy" refer to a straight or branched alkoxy group containing from 1 to 4 carbon atoms, such as methoxy, ethoxy, n-propoxy, isopropoxy, n-butoxy, isobutoxy, t-butoxy, etc;

e) the term "substituted phenyl" refers to:

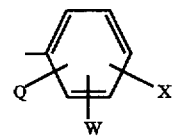

wherein Q, W, and X are independently chosen from the group consisting of: hydrogen, $C_1$–$C_4$ alkyl, $C_1$–$C_4$ alkoxy, halogen, —NHC(O)CH$_3$, amino, or hydroxy;

f) the term "pharmaceutically acceptable salts thereof" refers to either an acid addition salt or a basic addition salt.

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by Formula I or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

As is readily apparent to those skilled in the art, the compounds of Formula I in which A is NH will exist as tautomers. Any reference to the compounds of Formula I or an intermediate thereof should be construed as referring to either tautomer. These tautomers may be depicted as:

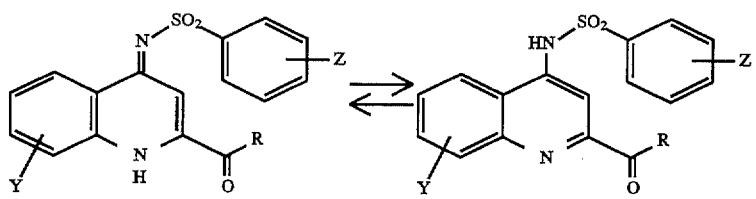

10

Examples of compounds encompassed by the present invention include the following. This list is meant to be representative only and is not intended to be exhaustive of the compounds encompassed within the scope of the invention:

5,7-Dichloro-2-acetyl-4-[benzenesulfonylimino]-1,4-dihydroquinoline;
5,7-Dichloro-2-benzoyl-4-[benzenesulfonylimino]-1,4-dihydroquinoline;
5,7-Dichloro-2-(4-aminobenzoyl)-4-[benzenesulfonylimino]-1,4-dihydroquinoline;
5,7-Dichloro-2-(2-aminobenzoyl)-4-[benzenesulfonylimino]-1,4-dihydroquinoline;
7-Chloro-2-acetyl-4-[benzenesulfonylimino]-1,4-dihydroquinoline;
7-Chloro-2-benzoyl-4-[benzenesulfonylimino]-1,4-dihydroquinoline;
2-Acetyl-4-[benzenesulfonylimino]-1,4-dihydroquinoline;
2-Benzoyl-4-[benzenesulfonylimino]-1,4-dihydroquinoline;
2-Benzoyl-4-[benzenesulfonylimino]-4H-chromene;
2-(4-Methoxybenzoyl)-4-[benzenesulfonylimino]-4H-chromene;
2-(4-Hydroxybenzoyl)-4-[benzenesulfonylimino]-4H-chromene;
5,7-Dichloro-2-benzoyl-4-[benzenesulfonylimino]-4H-chromene;
2-Benzoyl-4-[benzenesulfonylimino]-4H-thiochromene;
5,7-Dichloro-2-benzoyl-4-[benzenesulfonylimino]-4H-thiochromene;
5,7-Dichloro-2-acetyl-4-[(4-chlorobenzene)sulfonylimino]-1,4-dihydroquinoline;
5,7-Dichloro-2-benzoyl-4-[(4-methoxybenzene)sulfonylimino]-1,4-dihydroquinoline;
7-Chloro-2-acetyl-4-[(4-bromobenzene)sulfonylimino]-1,4-dihydroquinoline;
7-Chloro-2-benzoyl-4-[(2-chlorobenzene)sulfonylimino]-1,4-dihydroquinoline;
2-Acetyl-4-[(4-methylbenzene)sulfonylimino]-1,4-dihydroquinoline;
2-Benzoyl-4-[(4-chlorobenzene)sulfonylimino]-4H-chromene;
5,7-Dichloro-2-benzoyl-4-[(4-methylbenzene)sulfonylimino]-4H-chromene;

A general synthetic procedure for preparing these compounds of Formula I, in which A is NH, is set forth in Scheme A. The reagents and starting materials are readily available to one of ordinary skill in the art. In Scheme A, all substituents, unless otherwise indicated, are as previously defined.

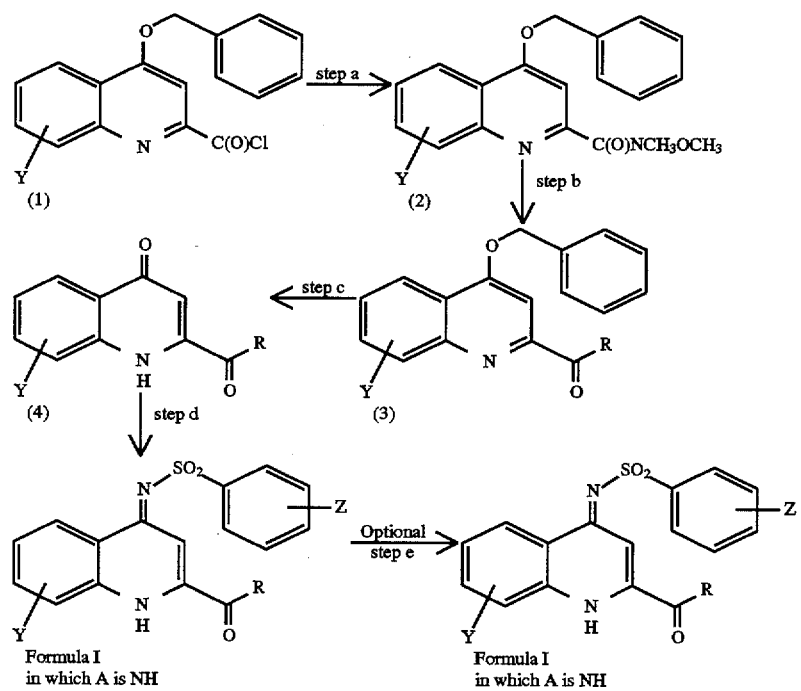

In Scheme A, step a, an appropriate acid chloride of structure (1), known analogously in the art [P. Leeson, European Patent Application No. 0 303 387, published Feb. 15, 1989], is converted to a N-methyl-O-methyl hydroxamic acid of structure (2).

An appropriate acid chloride of structure (1) is one in which Y is as desired in the final product of Formula I.

For example, an appropriate acid chloride of structure (1) is contacted with N-methyl-O-methyl hydroxylamine or a salt of N-methyl-O-methyl hydroxylamine. The reaction is carried out in the presence of a suitable base, such as triethylamine. The quantity of base used is one molar equivalent to neutralize the acid liberated in the reaction and in those reactions in which a salt of N-methyl-O-methyl hydroxylamine is used, an additional one molar equivalent is used to neutralize the salt of N-methyl-O-methyl hydroxylamine. The reaction is carried out in a suitable solvent, such as tetrahydrofuran (THF). The product is isolated by techniques well known in the art, such as evaporation in vacuo and extraction and can be purified by chromatography and recrystallization to give a compound of structure (2).

In Scheme A, step b, a N-methyl-O-methyl hydroxamic acid of structure (2) is contacted with an appropriate organometallic reagent to give after workup a ketone of structure (3).

An appropriate organometallic reagent is one of the structure R-Metal in which R is as desired in the final product of the Formula I.

For example, a compound of structure (2) is contacted with a suitable organometallic reagent. As is appreciated by one of ordinary skill in the art a suitable organometallic reagent can be chosen from the following: organolithium reagents, organosodium reagents, organopotassium reagents, organomagnesium reagents, organocadmium reagents, organozinc reagents, organomanganese reagents, etc., with organolithium reagents, organosodium reagents, organopotassium reagents, and organomagnesium reagents being preferred and organolithium reagents, and organomagnesium reagents being most preferred. The reaction is carried out in a suitable solvent, such as tetrahydrofuran or diethyl ether, at a temperature of from −78° C. to the reflux temperature of the solvent. The product can be isolated by techniques well known in the art, such as extraction and evaporation in vacuo. The product can then be purified by techniques well known in the art, such as chromatography or recrystallization to give a compound of structure (3).

In Scheme A, step c, a compound of structure (3) is debenzylated to give a compound of structure (4).

For example, a compound of structure (3) is contacted with a suitable debenzylating agent, such as trifluoroacetic acid, at a temperature that is sufficient to remove the protecting group but does not degrade the starting material or product. For debenzylation in which the suitable debenzylating agent is trifluoroacetic acid a temperature of from 70° C. to 80° C. is preferred. The product can be recovered and purified by techniques well known in the art, such as evaporation in vacuo, chromatography, and recrystallization to give a compound of structure (4).

In Scheme A, step d, a compound of structure (4) is contacted with an appropriate benzenesulfonyl isocyanate to form a benzenesulfonylimine of Formula I in which A is NH.

An appropriate benzenesulfonyl isocyanate is one in which Z is as desired in the final product of Formula I.

For example, a compound of structure (4) is contacted with a suitable benzenesulfonyl isocyanate. The reaction is carried out using from one to two molar equivalents of a suitable benzenesulfonyl isocyanate. The reaction is carried out in a suitable solvent, such as acetonitrile or propionitrile at temperatures of 20° C. to the refluxing temperature of the solvent. The product is recovered by techniques well known in the art, such as quenching with a protic solvent, such as methanol and evaporation in vacuo. The product can be purified by chromatography and recrystallization to give a compound of Formula I in which A is NH.

In Scheme A optional step e, a protected amino or protected hydroxy group may be deprotected to give compounds of Formula I in which R is a substituted phenyl in which Q, W, or X is amino or hydroxy. The selection of suitable protecting groups is well known in the art and the removal of protecting groups is described in *Protecting Groups in Organic Synthesis* by T. Greene.

The following examples present typical syntheses as described in Scheme A. These examples are understood to be illustrative only and are not intended to limit the scope of the invention in any way. As used in the following examples, the following terms have the meanings indicated: "g" refers to grams, "mg" refers to milligrams, "mmol" refers to millimoles, "mL" refers to milliliters, "°C." refers to degrees Celsius, "$R_f$" refers to retention; "mp" refers to melting point, "dec" refers to decomposition, "TLC" refers to thin layer chromatography.

EXAMPLE 1

Scheme A, step a:
5,7-Dichloro-4-benzyloxyquinoline-2-(N-methyl-O-methyl) hydroxamic acid Combine 5,7-dichloro-4-benzyloxyquinoline-2-carboxylic acid chloride (5.49 g, 15 mmol), triethylamine (4.17 mL, 30 mmol) and N-methyl-O-methylhydroxylamine hydrochloride (1.46 g, 15 mmol) in THF (150 mL). After 2 hours evaporate in vacuo and chromatograph the residue on a column of silica gel eluting with 5% acetone in dichloromethane. Recrystallize from ethyl acetate/hexane to give the title compound; mp, 109°–110° C. $R_f$=0.31 TLC/silica gel/5% acetone in dichloromethane. Elem. Anal. Calcd. for $C_{19}H_{16}Cl_2N_2O_3$: C, 58.32; H, 4.12; N, 7.16. Found: C, 58.40; H, 4.19; N, 7.08.

EXAMPLE 2

Scheme A, step b:
5,7-Dichloro-4-benzyloxy-2-benzoylquinoline

Combine 5,7-dichloro-4-benzyloxyquinoline-2-(N-methyl-O-methyl)hydroxamic acid (1.19 g, 3.1 mmol) and THF (30 mL) and cool to 0° C. Add dropwise phenylmagnesium bromide (1.2 mL, 3M, 3.3 mmol). Allow to stir for 15 minutes and then partition the reaction mixture between dichloromethane (200 mL) and water. Separate the organic layer and extract with 1M hydrochloric acid. Dry the organic layer over $MgSO_4$, filter, and evaporate in vacuo. Recrystallize from ethyl acetate/hexane to give the title compound; mp, 153°–154° C. Elem. Anal. Calcd. for $C_{23}H_{15}Cl_2NO_2$: C, 67.66; H, 3.70; N, 3.43. Found: C, 67.60; H, 3.76; N, 3.38.

EXAMPLE 3

Scheme A, step b:
5,7-Dichloro-4-benzyloxy-2-acetylquinoline

Combine 5,7-dichloro-4-benzyloxyquinoline-2-(N-methyl-O-methyl)hydroxamic acid (1.95 g, 5.0 mmol) and THF (25 mL) and cool to 0° C. Add dropwise methylmagnesium bromide (5.0 mL, 1M, 5.0 mmol). Allow to stir for 15 minutes and then pour the reaction mixture into dichloromethane (200 mL) and extract with 1M hydrochloric acid. Dry the organic layer over $MgSO_4$, filter, and evaporate in vacuo. Chromatograph the residue on a column of silica gel eluting with dichloromethane to give a solid. Recrystallize the solid from ethyl acetate/hexane to give the title compound; mp, 156°–157° C. Elem. Anal. Calcd. for $C_{18}H_{13}Cl_2NO_2$: C, 62.44; H, 3.78; N, 4.05. Found: C, 62.48; H, 3.84; N, 4.02.

EXAMPLE 4

Scheme A, step c:
5,7-Dichloro-2-benzoyl-1,4-dihydroquinol-4-one

Combine 5,7-dichloro-4-benzyloxy-2-benzoylquinoline (1.07 g, 2.6 mmol) and trifluoroacetic acid (65 mL) and heat to 70° C. After 4 hours evaporate the reaction mixture in vacuo to give a residue. Recrystallize the residue from acetonitrile to give the title compound; mp, 242°–243° C. $R_f$=0.33 TLC/silica gel/2% acetone in dichloromethane. Elem. Anal. Calcd. for $C_{16}H_9Cl_2NO_2$: C, 60.40; H, 2.85; N, 4.40. Found: C, 60.35; H, 2.89; N, 4.50.

EXAMPLE 5

Scheme A, step c:
5,7-Dichloro-2-acetyl-1,4-dihydroquinol-4-one

Combine 5,7-dichloro-4-benzyloxy-2-acetylquinoline (0.75 g, 2.2 mmol) and trifluoroacetic acid (55 mL) and heat to 80° C. After 4 hours evaporate the reaction mixture in vacuo to give a residue. Recrystallize the residue from acetonitrile to give the title compound; mp, 277°–278° C. (dec). $R_f$=0.29 TLC/silica gel/5% acetone in dichloromethane. Elem. Anal. Calcd. for $C_{11}H_7Cl_2NO_2$: C, 51.59; H, 2.76; N, 5.47. Found: C, 50.65; H, 2.83; N, 5.26.

EXAMPLE 6

Scheme A, step d:
5,7-Dichloro-2-benzoyl-4-[benzenesulfonylimino]-1,4-dihydroquinoline Combine 5,7-dichloro-2-benzoyl-1,4-dihydroquinolin-4-one (0.57 g, 1.8 mmol) and benzenesulfonyl isocyanate (0.26 mL, 2.0 mmol) in acetonitrile (9 mL) and heat at reflux for 18 hours. Add methanol (5 mL) to quench the reaction. Evaporate in vacuo to obtain a residue. Chromatograph the residue on a column of silica gel eluting with dichloromethane to obtain a solid. Recrystallize the solid from ethyl acetate/hexane to give the title compound; mp, 186°–187° C. $R_f$=0.37 TLC/silica gel/dichloromethane. Elem. Anal. Calcd. for $C_{22}H_{14}Cl_2N_2O_3S$: C, 57.77; H, 3.09; N, 6.13. Found: C, 57.76; H, 3.22; N, 5.91.

EXAMPLE 7

Scheme A, step d:
5,7-Dichloro-2-acetyl-4-[benzenesulfonylimino]-1,4-dihydroquinoline Combine 5,7-dichloro-2-acetyl-1,4-dihydroquinol-4-one (0.28 g, 1.1 mmol) and benzenesulfonyl isocyanate (0.16 mL, 1.2 mmol) in acetonitrile (5 mL). Heat at reflux for 3 hours. Add methanol (5 mL) to quench the reaction. Evaporate in vacuo to obtain a residue. Chromatograph the residue on a column of silica gel eluting with dichloromethane to obtain a solid. Recrystallize the solid from ethyl acetate/hexane to give the title compound; mp, 163°–164° C. $R_f$=0.32 TLC/silica gel/dichloromethane. Elem. Anal. Calcd. for $C_{17}H_{12}Cl_2N_2O_3S$: C, 51.65; H, 3.04; N, 7.09. Found: C, 51.92; H, 3.11; N, 6.85.

A general synthetic procedure for preparing some of the compounds of Formula I, in which A is O or S is set forth in Scheme B. In Scheme B, all substituents, unless otherwise indicated, are as previously defined.

SCHEME B

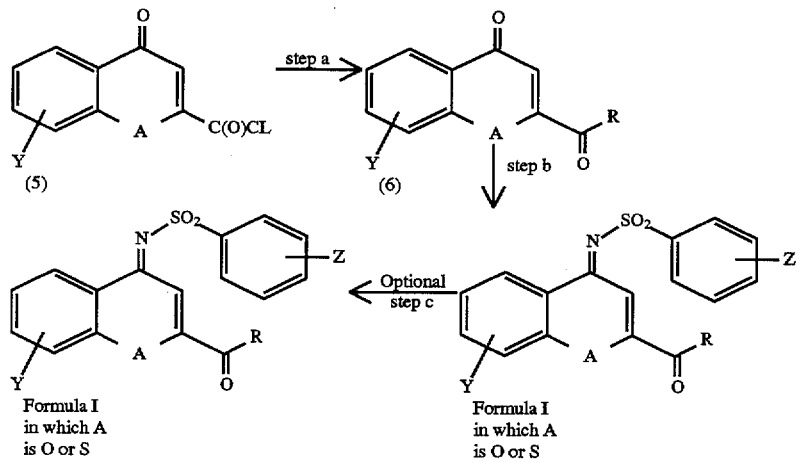

In Scheme B step a, an acid chloride of structure (5), [Chromenes, Chromanones, and Chromones, edited by G. P. Ellis (John Wiley & Sons 1977)] is subjected to a Friedel-Crafts reaction with benzene or an appropriately substituted benzene to give a compound of structure (6).

The use of benzene in this reaction gives a compound of structure (6) in which R is phenyl and gives rise to compounds of Formula I in which R is phenyl.

The use of an appropriately substituted benzene in this reaction gives a compound of structure (6) in which R is a substituted phenyl and gives rise to compounds of Formula I in which R is a substituted phenyl. An appropriate substituted benzene contains Q, W, and X as are desired in the final product of Formula I or contains Q, W, and X which are a protected amino, such as the acetyl group of acetanilide or protected hydroxy, such as the methyl group of anisole. These protecting groups can be removed to give rise to substituents Q, W, and X which are amino and hydroxy as desired in the final product of Formula I.

For example, an acid chloride of structure (5) is contacted with benzene or an appropriately substituted benzene. The reaction in which an acid chloride of structure (5) is contacted with benzene is carried out using the benzene as the solvent. The reaction in which an acid chloride of structure (5) is contacted with an appropriately substituted benzene the appropriately substituted benzene may be used as the solvent. Alternately, the reaction may be carried out in a solvent, such as nitrobenzene, nitromethane, dichloromethane, or carbon tetrachloride. The reaction is carried out in the presence of a molar excess of a suitable catalyst, such as aluminum trichloride, aluminum tribromide, zinc chloride, zinc bromide, stannic chloride, boron trifluoride, and the like. The selection and use of catalysts in the Friedel-Crafts reaction is well known and appreciated in the art. The reaction can be carried out at temperatures of between 0° C. and the refluxing temperature of the solvent. The product may be obtained from the reaction zone by methods that are well known in the art, such as pouring the reaction mixture onto ice or into ice-water and isolation of the product by filtration or by extraction into a suitable organic solvent, such as ethyl acetate, diethyl ether, or dichloromethane. The product can be purified by chromatography and recrystallization to give a compound of structure (6).

In Scheme B step b, the compound of structure (6) is contacted with an appropriate benzenesulfonyl isocyanate to give a benzenesulfonylimine of Formula I in which A is O or S.

An appropriate benzenesulfonyl isocyanate is one in which Z is as desired in the final product of Formula I.

For example, the compound of structure (6) is contacted with a suitable benzenesulfonyl isocyanate. The reaction is carried out in a suitable solvent, such as acetonitrile or propionitrile at temperatures of 20° C. to the refluxing temperature of the solvent. The product is recovered by techniques well known in the art, such as evaporation in vacuo, chromatography, and recrystallization to give a compound of Formula I in which A is O or S.

In Scheme B optional step c, a protected amino or protected hydroxy group may be deprotected to give compounds of Formula I in which R is a substituted benzene and Q, W, or X is amino or hydroxy. The selection of suitable protecting groups is well known in the art and the removal of protecting groups is described in *Protecting Groups in Organic Synthesis* by T. Greene.

The following examples present typical syntheses as described in Scheme B. These examples are understood to be illustrative only and are not intended to limit the scope of the invention in any way. As used in the following examples, the following terms have the meanings indicated: "g" refers to grams, "mmol" refers to millimoles, "mL" refers to milliliters, "°C." refers to degrees Celsius, "$R_f$" refers to retention "mp" refers to melting point.

EXAMPLE 8

Scheme B, Step a:
2-Benzoyl-chromone

Combine chromone-2-carboxylic acid chloride (2.0 g, 9.6 mmol) and aluminum chloride (3.84 g, 28.7 mmol) in benzene (70 mL). Heat at reflux for 4 hours. Pour the reaction mixture into ice-water (150 mL). Extract with dichloromethane twice. Dry the separated organic layers over $MgSO_4$, filter, and evaporate in vacuo. Chromatograph on silica gel eluting with 15% ethyl acetate/hexane. Evaporate the product containing fractions to give the title compound as a solid.

EXAMPLE 9

Scheme B, step a:
2-(4-Methoxybenzoyl)-chromone

Combine chromone-2-carboxylic acid chloride (10 mmol), and aluminum chloride (30 mmol) in anisole (70 mL). Heat at reflux for 24 hours. Pour the reaction mixture into ice-water (150 mL). Extract twice with dichloromethane. Dry the separated organic layers over $MgSO_4$, filter, and evaporate in vacuo. Chromatograph on silica gel to give the title compound.

EXAMPLE 10

Scheme Br step b:
2-Benzoyl-4-benzenesulfonylimino-4H-chromene

Combine 2-Benzoyl-chromone (0.17 g, 0.68 mmol) and benzenesulfonyl isocyanate (1.02 mL, 2.03 mmol) in acetonitrile (7.0 mL). Heat at reflux for 48 hours. Add methanol (5 mL) to quench the reaction. Evaporate in vacuo to obtain a solid. Recrystallize from methanol to give the title compound as a solid: mp, 159°–160° C. Elem. Anal calcd. for $C_{22}H_{15}NO_4S$: C, 67.85; H, 3.88; N, 3.60. Found: C, 67.47; H, 3.70; N, 3.56.

EXAMPLE 11

Scheme B, step b:
2-(4-Methoxybenzoyl)-4-benzenesulfonylimino-4H-chromene

Combine 2-(4-methoxybenzoyl)-chromone (1 mmol) and benzenesulfonyl isocyanate (1.2 mmol) in acetonitrile (7.0 mL). Heat at reflux for 48 hours. Add methanol (5 mL) to quench the reaction. Evaporate in vacuo. Recrystallize to give the title compound.

EXAMPLE 12

Scheme B, optional step c:
2-(4-hydroxybenzoyl)-4-benzenesulfonylimino-4H-chromene Combine 2-(4-methoxybenzoyl)-4-benzenesulfonylimino-4H-chromene (1 mmol) and sodium thioethoxide (2 mmol) in dimethylformamide (5 mL). Stir for 48 hours. Dilute the reaction mixture with water and dichloromethane. Separate the organic layer, dry over $MgSO_4$, filter, and evaporate in vacuo. Chromatograph on silica gel to give the title compound.

A general synthetic procedure for preparing some of the compounds of Formula I, in which A is NH is set forth in Scheme C. In Scheme C, all substituents, unless otherwise indicated, are as previously defined.

SCHEME C

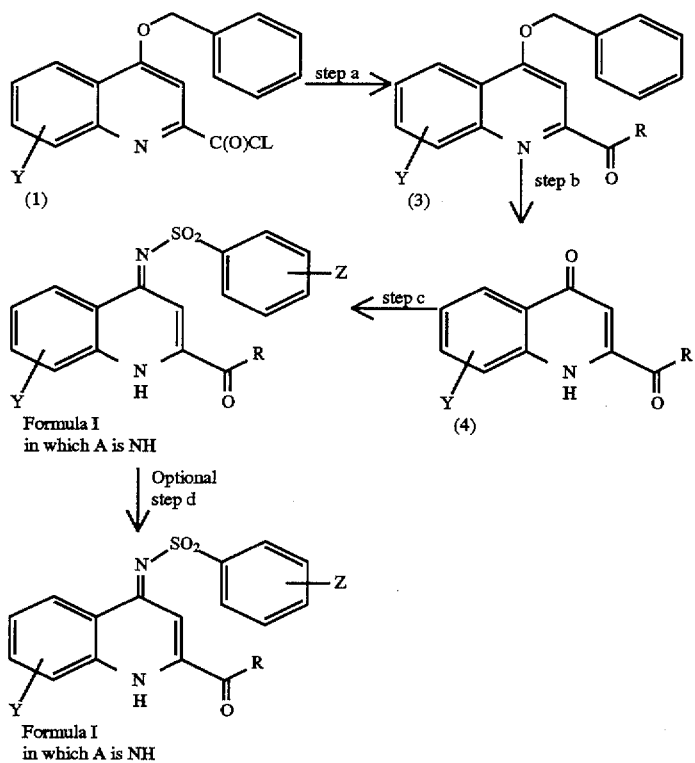

Formula I
in which A is NH

In Scheme C, step a, an appropriate acid chloride of structure (1), known analogously in the art [P. Leeson, European Patent Application No. 0 303 387, published Feb. 15, 1989], is reacted with an appropriate organostannane in the presence of a catalyst to give compounds of structure (3).

An appropriate acid chloride of structure (1) is one in which Y is as desired in the final product of Formula I.

An appropriate organostannane is one that provides a group R as is desired in the final product of Formula I. When R is a substituted phenyl the substituents Q, W, or X are as desired in the final product of Formula I. Alternately, an appropriate organostannane is one that provides an group R containing a protected amino group or a protected hydroxy group which give rise to Q, W, or X which are amino or hydroxy as desiPed in the final product of Formula I.

For example, an appropriate acid chloride of structure (1) is contacted with an appropriate organostannane in the presence of a catalyst, such as tetrakis(triphenylphosphine) palladium (0), bis(acetonitrile)palladium (II) chloride, palladium (II) chloride, palladium (II) acetate, palladium (II) bromide, bis(benzonitrile)palladium (II) chloride, palladium (II) acetoacetate. The reaction is carried out in a solvent such as, tetrahydrofuran, 1-methyl-2-pyrrolidinone, or dimethylformamide. The reaction is carried out at temperature of from 0° C. to the refluxing temperature of the solvent. The reaction requires from 1 to 72 hours and should be stopped at a time that maximizes the desired product (3) and minimizes undesired products. The product is isolated from the reaction zone and purified by techniques well known in the art, such as evaporation, extraction, chromatography, and recrystallization.

In Scheme C step b, compound of structure (3) is debenzylated to give a compound of structure (4).

For example, a compound of structure (3) is contacted with a suitable debenzylating agent, such as trifluoroacetic acid, at a temperature that is sufficient to remove the protecting group but does not degrade the starting material or product. In debenzylations in which the suitable debenzylating agent is trifluoroacetic acid a temperature of 70° C. to 80° C. is preferred. This reaction may remove acid labile protecting groups when the group R contains a protected amino or protected hydroxy group. In those reactions where a protecting group is removed by the debenzylating conditions the reaction mixture is evaporated in vacuo and the protecting group is reintroduced on the crude reaction mixture by methods well known in the art and described in *Protecting Groups in Organic Synthesis* by T. Greene. The product is recovered by techniques well known in the art, such as evaporation in vacuo, chromatography, and recrystallization to give a compound of structure (4).

In Scheme C, step c, a compound of structure (4) is contacted with an appropriate benzenesulfonyl isocyanate to a benzenesulfonylimine of Formula I.

An appropriate benzenesulfonyl isocyanate is one in which Z is as desired in the final product of Formula I.

For example, a compound of structure (4) is contacted with a suitable benzenesulfonyl isocyanate. The reaction is carried out in a suitable solvent, such as acetonitrile or propionitrile at temperatures of 20° C. to the refluxing temperature of the solvent. The product is recovered by techniques well known in the art, such as evaporation in vacuo, chromatography, and recrystallization to give a compound of Formula I in which A is NH.

In Scheme C optional step d, a protected amino or protected hydroxy group may be deprotected to give compounds of Formula I in which R is a substituted phenyl and Q, W, or x are amino or hydroxy. The selection of suitable protecting groups is well known in the art and the removal of protecting groups is described in *Protecting Groups in Organic Synthesis* by T. Greene.

The following examples present typical syntheses as described in Scheme C. These examples are understood to be illustrative only and are not intended to limit the scope of the invention in any way. As used in the following examples, the following terms have the meanings indicated: "g" refers to grams, "mg" refers to milligrams, "mmol" refers to millimoles, "mL" refers to milliliters, "°C." refers to degrees Celsius, "$R_f$" refers to retention "mp" refers to melting point, "dec" refers to decomposition, "TLC" refers to thin layer chromatography.

EXAMPLE 13

Preparation of 4-Tributylstannyl-N,N'-(1,1,4,4-tetramethyl-1,4-disilethylene)aniline 4-Tributylstannyl-N,N'-(1,1,4,4-tetramethyl-1,4-disilethylene)aniline Combine 4-bromo-N,N'-(1,1,4,4-tetramethyl-1,4-disilethylene)aniline (10 mmol) [T. L. Guggenheim, *Tet. Lets.* 25, 1253–1254 (1984)] and hexabutylditin (20 mmol) in toluene (50 mL). Add tris(dibenzylideneacetone)-dipalladium(0) (400 mg) and heat to 80° C. under an inert atmosphere. After 48 hours, evaporate in vacuo and purify by chromatography on silica gel to give the title compound.

EXAMPLE 14

Scheme C, step a:
5,7-Dichloro-2-[[4-N,N'-(1,1,4,4-tetramethyl-1,4-disilethylene)amino]benzoyl]-4-benzyloxyquinoline Combine 5,7-dichloro-4-benzyloxyquinoline-2-acid chloride (1.83g, 5mmol) and 4-tributylstannyl-N,N'-(1,1,4,4-tetramethyl-1,4-disilethylene)aniline (5 mmol) in 1-methyl-2-pyrrolidinone (5 mL) and add bis-acetonitrilepalladium (II) dichloride (5 mg). Flush the vessel with nitrogen gas, seal, and heat to 60° C. After stirring for 8 hours add more bis-(acetonitrile)palladium (II) dichloride (2.07 mg, 0.08 mmol) and continue stirring for 16 hours. Pour the reaction mixture into water and extract with dichloromethane, dry over magnesium sulfate and evaporate in vacuo. Chromatograph on silica gel to give the title compound.

EXAMPLE 15

Scheme C, step a:
5,7-Dichloro-2-[2-(t-butoxycarbonylamino)benzoyl]-4-benzyloxyquinoline Combine 5,7-dichloro-4-benzyloxyquinoline-2-acid chloride (1.83 g, 5 mmol) and 2-(t-butoxycarbonylamino) phenyltrimethylstannane (5 mmol) [F. G. Salituro and I. A. McDonald, *J. Org. Chem.* 53, 6138–6139 (1988)] in toluene (5 mL) and add tetrakis(tri-phenylphosphine) palladium (0) (5 mg). Flush the vessel with nitrogen gas, seal, and heat to 60° C. After stirring for 8 hours add more bis-(acetonitrile) palladium (II) dichloride (2.07 mg, 0.08 mmol) and continue stirring for 16 hours. Pour the reaction mixture into water and extract with dichloromethane, dry over magnesium sulfate and evaporate in vacuo. Chromatograph on silica gel to give the title compound.

EXAMPLE 16

Scheme C, step b:
5,7-Dichloro-2-[[4-N,N'-(1,1,4,4-tetramethyl-1,4-disilethylene) amino]benzoyl]-1,4-dihydroquinol-4-one Combine 5,7-dichloro-2-[[4-N,N'-(1,1,4,4-tetramethyl-1,4-disilethylene)amino]benzoyl]-4-benzyloxyquinoline (4 mmol) and trifluoroacetic acid (55 mL) and heat to 80° C. After 4 hours evaporate the reaction mixture in vacuo to give a residue. Recrystallize the residue from acetonitrile to give the title compound.

EXAMPLE 17

Scheme C, step b:
5,7-Dichloro-2-[2-(t-butoxycarbonylamino)benzoyl]-1,4-dihydroquinol-4-one Combine 5,7-dichloro-2-[2-(t-butoxycarbonylamino) benzoyl]-4-benzyloxyquinoline (4 mmol) and trifluoroacetic acid (55 mL) and heat to 80° C. After 4 hours evaporate the reaction mixture in vacuo to give a residue. Add dichloromethane and evaporate several times to completely remove residual trifluoroacetic acid. Dissolve the crude reaction mixture in dichloromethane (20 mL) and add di-t-butyl dicarbonate (4 mmol). Allow to stir for 24 hours. Evaporate in vacuo. Chromatograph on silica gel to give the title compound.

EXAMPLE 18

Scheme C, step c:
5,7-Dichloro-2-[[4-N,N'-(1,1,4,4-tetramethyl-1,4-disilethylene) amino]benzoyl]-4-[benzenesulfonylimino]-1,4-dihydroquinoline Combine 5,7-dichloro-2-[[4-N,N'-(1,1,4,4-tetramethyl-1,4-disilethylene) amino]benzoyl]-1,4-dihydroquinolin-4-one (2 mmol) and benzenesulfonyl isocyanate (2.2 mmol) in acetonitrile (9 mL) and heat at reflux for 48 hours. Add methanol (5 mL) to quench the reaction. Evaporate in vacuo to obtain a residue. Chromatograph the residue on a column of silica gel to give the title compound.

EXAMPLE 19

Scheme C, step b:
5,7-Dichloro-2-[2-(t-butoxycarbonylamino)benzoyl]-4-[benzenesulfonylimino]-1,4-dihydroquinoline Combine 5,7-dichloro-2-[2-(t-butoxycarbonylamino) benzoyl]-1,4-dihydroquinol-4-one (2 mmol) and benzenesulfonyl isocyanate (2.2 mmol) in acetonitrile (9 mL) and heat at reflux for 48 hours. Add methanol (5 mL) to quench the reaction. Evaporate in vacuo to obtain a residue. Chromatograph the residue on a column of silica gel to give the title compound.

EXAMPLE 20

Scheme C, optional step d:
5,7-Dichloro-2-(4-aminobenzoyl)-4-[benzenesulfonylimino]-1,4-dihydroquinoline Combine 5,7-dichloro-2-[[4-N,N'-(1,1,4,4-tetramethyl-1,4-disilethylene) amino]benzoyl]-4-[benzenesulfonylimino]-1,4-dihydroquinoline (1 mmol) and tetrabutylammonium fluoride (1.2 mL, 1M in tetrahydrofuran, 1.2 mmol) in tetrahydrofuran (5 mL). Stir for 24 hours. Evaporate in vacuo to obtain a residue. Chromatograph the residue on a column of silica gel to give the title compound.

EXAMPLE 21

Scheme C, optional step d:
5,7-Dichloro-2-(2-aminobenzoyl)-4-[benzenesulfonylimino]-1,4-dihydroquinoline Combine 5,7-dichloro-2-[2-(t-butoxycarbonylamino) benzoyl]-4-[benzenesulfonylimino]-1,4-dihydroquinoline (1 mmol) and ethyl acetate (50 mL). Add trifluoroacetic acid (1 mL) and stir. After 24 hours, evaporate in vacuo and partition the residue between dichloromethane and a saturated aqueous sodium bicarbonate solution. Separate the organic layer, dry over MgSO₄, filter and evaporate in vacuo. Chromatograph the residue on a column of silica gel to give the title compound.

A general synthetic procedure for preparing some of the compounds of Formula I, in which A is O and S is set forth in Scheme D. In Scheme D, all substituents, unless otherwise indicated, are as previously defined.

In Scheme D, step a, an acid chloride of structure (5), which is well known in the art, is reacted with an appropriate organostannane in the presence of a catalyst to give a compound of structure (6).

An appropriate acid chloride of structure (5) is one in which Y is as desired in the final product of Formula I.

An appropriate organostannane is one that provides a group R as is desired in the final product of Formula I. When R is a substituted phenyl the substituents Q, W, or X are as desired in the final product of Formula I. Alternately, an appropriate organostannane is one that provides an group R containing a protected amino group or a protected hydroxy group which give rise to Q, W, or X which are amino or hydroxy as desired in the final product of Formula I.

For example, an appropriate acid chloride of structure (5) is contacted with an appropriate organostannane in the presence of a catalyst, such as tetrakis(tri-phenylphosphine) palladium (0), bis(acetonitrile)palladium (II) chloride, palladium (II) chloride, palladium (II) acetate, palladium (II) bromide, bis(benzonitrile)palladium (II) chloride, palladium (II) acetoacetate. The reaction is carried out in a solvent such as, tetrahydrofuran, 1-methyl-2-pyrrolidinone, or dimethylformamide. The reaction is carried out at temperature of from 0° C. to the refluxing temperature of the solvent. The reaction requires from 1 to 72 hours and should be stopped at a time that maximizes the desired product (3) and minimizes undesired products. The product is isolated from the reaction zone by methods that are well known in the art, such as extraction and evaporation. The product can be purified by chromatography or recrystallization to give a compound of structure (6).

In Scheme D step b, a compound of structure (6) is contacted with an appropriate benzenesulfonyl isocyanate to a benzenesulfonylimine of Formula I in which A is O or S.

An appropriate benzenesulfonyl isocyanate is one in which Z is as desired in the final product of Formula I.

For example, a compound of structure (6) is contacted with a suitable benzenesulfonyl isocyanate. The reaction is carried out in a suitable solvent, such as acetonitrile or propionitrile at temperatures of 20° C. to the refluxing temperature of the solvent. The product is recovered by techniques well known in the art, such as evaporation in vacuo, chromatography, and recrystallization to give a compound of Formula I in which A is O or S.

In Scheme D optional step c, a protected amino or hydroxy group may be deprotected to give compounds of Formula I in which R is a substituted phenyl and Q, W, or

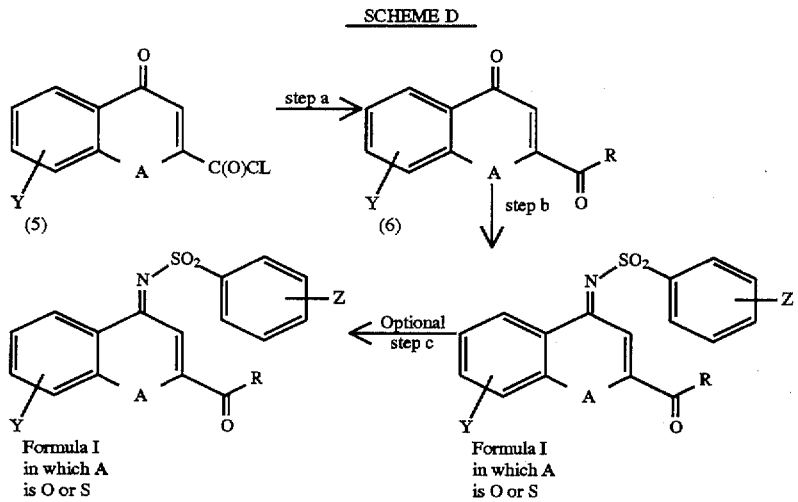

SCHEME D x is amino or hydroxy. The selection of suitable protecting groups is well known in the art and the removal of protecting groups is described in *Protecting Groups in Organic Synthesis* by T. Greene.

The following examples present typical syntheses as described in Scheme D. These examples are understood to be illustrative only and are not intended to limit the scope of the invention in any way. As used in the following examples, the following terms have the meanings indicated: "g" refers to grams, "mg" refers to milligrams, "mmol" refers to millimoles, "mL" refers to milliliters, "° C." refers to degrees Celsius, "$R_f$" refers to retention "mp" refers to melting point, "dec" refers to decomposition, "TLC" refers to thin layer chromatography.

EXAMPLE 22

Scheme D, step a:
2-[[4-N,N'-(1,1,4,4-tetramethyl-1,4-disilethylene)amino]benzoyl]-chromone Combine chromone-2-carboxylic acid chloride (10 mmol) and 4-tributylstannyl-N,N'-(1,1,4,4-tetramethyl-1,4-disilethylene)aniline (5 mmol) in 1-methyl-2-pyrrolidinone (5 mL) and add bis-acetonitrilepalladium (II) dichloride (5 mg). Flush the vessel with nitrogen gas, seal, and heat to 60° C. After stirring for 8 hours add more bis-(acetonitrile)palladium (II) dichloride (2.07 mg, 0.08 mmol) and continue stirring for 16 hours. Pour the reaction mixture into water and extract with dichloromethane, dry over MgSO₄, and evaporate in vacuo. Chromatograph on silica gel to give the title compound.

EXAMPLE 23

Scheme D, step b:
2-[[4-N,N'-(1,1,4,4-tetramethyl-1,4-disilethylene)amino]benzoyl]-4-benzenesulfonylimino-4H-chromene Combine 2-[[4-N,N'-(1,1,4,4-tetramethyl-1,4-disilethylene)amino]benzoyl]-chromone (1 mmol) and benzenesulfonyl isocyanate (1.2 mmol) in acetonitrile (7.0 mL). Reflux for 48 hours. Add methanol (5 mL) to quench the reaction. Evaporate in vacuo. Chromatograph on silica gel to give the title compound.

EXAMPLE 24

Scheme D, optional step c:
2-(4-Aminobenzoyl)-4-benzenesulfonylimino-4H-chromene Combine 2-[[4-N,N'-(1,1,4,4-tetramethyl-1,4-disilethylene)amino]benzoyl]-4-benzenebenzenesulfonylimine-4H-chromene (1 mmol) and tetrabutylammonium fluoride (1.2 mL, 1M in tetrahydrofuran, 1.2 mmol) in tetrahydrofuran (5 mL). Stir for 24 hours. Evaporate in vacuo to obtain a residue. Chromatograph the residue on a column of silica gel to give the title compound.

Interleukin-1 (IL-1) consists of two polypeptides, termed IL-1α and IL-1β, that belong to a family of cytokines that also includes tumor necrosis factor (TNFα) and IL-6. These cytokines have overlapping biological properties, including the ability to stimulate T and B lymphocytes and to effect the expression of proteins involved in many immunological and inflammatory responses.

Agents which inhibit IL-1 action may do so by several mechanisms including: inhibition of IL-1 production by inhibition of the expression, synthesis, or release of IL-1; antagonism at an IL-1 receptor; inhibition of the IL-1 induced amplification of IL-1 production; or inhibition of IL-1 induced the production of other cytokines; etc.

It is known, for example, that IL-1 is produced by epithelial cells and stimulates fibroblast proliferation and release of proteolytic enzymes (e.g. collagenase) and prostaglandins in inflammatory processes, i.e. rheumatoid arthritis. See Durom, S. K.; Schmidt, J. A.; Oppenheim, J. J.; Interleukin 1: an Immunological Perspective, *Ann. Rev. Immunol.* 3, 263–287 (1985), Otterness, I. G.; Bliven, M. L.; Downs, J. T.; Natoli, E. J.; Hanson, D. C.; Inhibition of Interleukin-1 Synthesis by Tenidap: a New Drug for Arthritis, *Cytokine*, 3, 277–283 (1991), and Miyasaka, N.; Sato, K.; Goto, M.; Sasano, M.; Natsuyma, M.; Inoue, K.; and Nishioks, K., Augmented Interleukin-1 Production and HLA-DR Expression in the Synovium of Rheumatoid Arthritis Patients, *Arthritis and Rheumatism*, 31, 480–486 (1988). Thus agents which inhibit IL-1 action would be useful in the treatment of rheumatoid arthritis.

It has also been shown that IL-1 may affect the pathogenesis of atherosclerosis directly, by stimulating smooth muscle cell proliferation or, indirectly, through the action of platelet-derived growth factor (PDGF). See Jackson, R. L. and Ku, G., Interleukin-1β, its Role in the Pathogenesis of Atherosclerosis and Agent that Inhibit its Action, *Current Drugs: Anti-atherosclerotic Agents*, pp. B31–B42 (October 1991). In addition, Tenidap, an agent known to block IL-1 production, reduces the total level of serum cholesterol, serum LDL cholesterol and serum triglycerides in a mammal having an arthritic condition for which Tenidap is being administered. See U.S. Pat. No. 5,122,534 (Feb. 8, 1991). Thus agents which inhibit IL-1 action may also be useful in the prophylactic treatment of atherosclerosis.

In addition, it has also been postulated that macrophages infiltrating the pancreatic islets may play a role in the destruction of β-cells and that cytokines, in particular IL-1, released locally from the macrophages may be the toxic molecules causing β-cell destruction in insulin-dependent diabetes mellitus (IDDM). See Sandlet, S., Eizirik, D., Svensson, C., Strandell, E., Welsh, M. and Welsh, N., Biochemical and Molecular Action of Interleukin 1 on Pancreatic β-Cells, *Autoimmunity*, 10, 241–253 (1991). Thus agents which inhibit IL-1 action may also be useful in the treatment of diabetes mellitus.

A correlation has also been shown between increased IL-1 production and the clinical course of multiple sclerosis (MS). It has been demonstrated that there is a significant increase in IL-1α production by cultured blood mononuclear cells for patients with MS, with patients in the active phase of relapsing MS showing the greatest increase in IL-1α production. See Matsuda, M., Tsukada, N., Miyagi, K., and Yanagisawa, N., Increased Interleukin-1 production by peripheral blood mononuclear cells in patients with multiple sclerosis, *Journal of the Neurological Sciences*, 102, 100–104 (1991). Thus agents which inhibit IL-1 action may also be useful in the treatment of multiple sclerosis.

Studies have also shown that IL-1 receptor antagonists might be useful for the treatment of incipient or established pulmonary fibrosis. See Piguet, P., Vesin, C., Grau, G., Thompson, R., Interleukin-1 Receptor Antagonist (IL-1ra) Prevents or Cures Pulmonary Fibrosis Elicited in Mice By Bleomycin or Silica, *Cytokine*, 5, 57–61 (1993). Thus agents which inhibit IL-1 action may also be useful in the treatment of pulmonary fibrosis.

It has also been suggested that interleukin-1 receptor antagonists may play a role in reducing mortality form septic shock. See Ohlsson, K., Bjork, P., Bergenfeldt, M., Hageman, R., and Thompson, R., Interleukin-1 Receptor Antagonist Reduces Mortality from Endotoxin Shock, *Nature*, 348, 550–552 (1990). Thus agents which inhibit IL-1 action may also be useful in the treatment of septic shock.

The compounds of Formula I inhibit IL-1 action. One mechanism for inhibiting IL-1 action is to inhibit IL-1 production. Inhibition of IL-1 production was tested using lipopolysaccharide (LPS) stimulated macrophages. Inhibition of IL-1 induced production of cytokines was tested by measuring the inhibition of TNFα (tumor necrosis factor alpha) synthesis from IL-1 stimulated macrophages. The protocols for these test procedures are described below.

Endotoxin-Induced Interleukin-1 Beta Release by Human Macrophages

Objective

The objective of this test is to determine the inhibitory concentrations for the test compounds against endotoxin-induced interleukin-1 beta (IL-1β) release (production) by human peripheral blood monocyte-derived macrophages.

Source

The source of the human peripheral blood monocyte-derived macrophages is as follows:

Venous blood is collected from healthy volunteers in 10 mM sodium citrate (2 mL sterile sodium citrate for 40 mL blood). Mononuclear cells are isolated with the Leucoprep tubes (Becton Dickenson, product number 2752 or 2751) spun at 1500 g for 15 minutes. Aliquots of $3 \times 10_6$ mononuclear cells are added to 24-well tissue culture plates (Corning) in RPMI-1640. After one hour incubation at 37° C., non-adherent cells are gently rinsed off. The adherent cells (macrophages) are given back fresh medium RPMI-1640, 1 mL/well.

Procedure

Macrophage monolayer cultures are pretreated with compounds one hour prior to endotoxin (20 ng/mL, *Salmonella typhimurium*, Re-mutant, from Ribi Immuchem.) stimulation. Compounds dissolved in 95% ethanol or DMSO would require additional monolayer cultures treated with 10 or 2.5 μl 95% ethanol or DMSO, respectively. Culture supernatants are collected 24 hours later and are tested for IL-1β using a commercial ELISA kit (Cistron).

Analysis of Results

The IL-1β concentration in the culture supernatant is calculated by a standard curve generated from a series of known concentrations. Potency of compound is reported in $IC_{50}$ (μM).

Results:

| Compound | $IC_{50}$ |
| --- | --- |
| 5,7-Dichloro-2-benzoyl-4-[benzenesulfonylimino]-1,4-dihydroquinoline | 2 μM |
| 5,7-Dichloro-2-acetyl-4-[benzenesulfonylimino]-1,4-dihydroquinoline | 4 μM |

Interleukin-1-Beta-Induced Tumor Necrosis Factor Alpha Release by Human Macrophages Objective To determine the inhibitory concentrations for the test compounds against interleukin-1 beta (IL-1β)-induced tumor necrosis factor alpha (TNFα) release by human peripheral blood monocyte-derived macrophages. It should be understood that this is a test of the ability of the test compounds to modulate, i.e. inhibit, the activity of IL-1β by measuring the inhibition of IL-1β induced release of TNFα.

Source Human Peripheral Blood Monocyte-Derived Macrophages:

Venous blood is collected form healthy volunteers in 10 mM sodium citrate (2 mL sterile sodium citrate for 40 mL blood). Mononuclear cells are isolated with the Leucoprep tubes (Becton Dickinson, product number 2752 or 2751) spun at 1500 g for fifteen minutes. Aliquots of $3 \times 10_6$ mononuclear cells are added to 24-well tissue culture plates (Corning) in RPMI-1640. After 1 hour incubation at 37° C., non-adherent cells are gently rinsed off. The adherent cells (macrophages) are given back fresh medium RPMI-1640, 1 mL/well.

Procedure

Macrophage monolayer cultures are pretreated with compounds one hour prior to IL-1β (20 ng/mL, recombinant human IL-1β) stimulation. Compounds dissolved in 95% ethanol or DMSO would require additional monolayer cultures treated with 10 or 2.5 μl 95% ethanol or DMSO, respectively. Culture supernatants are collected 24 hours later and are tested for TNF-α using a commercial ELISA kit (Cistron).

Analysis of Results

The TNF-α concentration in the culture supernatant is calculated by a standard curve generated from a series of known concentrations. Potency of compound is reported in $IC_{50}$ (UM).

Results:

| Compound | $IC_{50}$ |
| --- | --- |
| 2-Benzoyl-5,7-dichloro-4-[benzenesulfonylimino]-1,4-dihydroquinoline | 3 μM |
| 2-Acetyl-5,7-dichloro-4-[benzenesulfonylimino]-1,4-dihydroquinoline | 8 μM |
| 2-Benzoyl-4-[benzenesulfonylimino]-4H-chromene | 1.3 μM |

The compounds of the present invention may be administered by a variety of routes. They are effective if administered orally. The compounds may also be administered parenterally (i.e. subcutaneously, intravenously, intramuscularly, intraperitoneally, or intrathecally).

In order to exhibit these therapeutic properties, the compounds need to be administered in a quantity sufficient to inhibit IL-1 action. The dosage range at which these compounds exhibit this inhibitory effect can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 0.1 mg/kg/day to about 50 mg/kg/day for any of the diseases or conditions listed above.

Pharmaceutical compositions can be manufactured utilizing techniques known in the art. Typically, an effective amount of the compounds of Formula I will be admixed with a pharmaceutically acceptable carrier.

For oral administration, the compounds of Formula I can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds of Formula I may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art.

As used in this application:

a) the "patient" refers to warm blooded animals such as, for example guinea pigs, mice, rats, cats, rabbits, dogs, monkeys, chimpanzees, and human;

b) the term "treat" refers to the ability of the compounds to either relieve, alleviate, or slow the progression of the patient's disease.

c) the term "an effective amount" refers to an amount which is effective, upon single or multiple dose administration to the patient, in inhibiting IL-1 action.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951; 3,797,494; 3,996,934; and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is nonporous. The pharmaceutically effective compound dissolves in and diffuses through the matrix itself. Release by microporous flow occurs when the pharmaceutically effective compound is transported through a liquid phase in the pores of the matrix.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art.

What is claimed is:

1. A compound of the formula

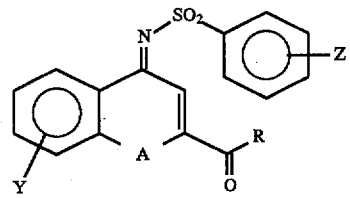

wherein

A is NH;

R is $C_1$–$C_6$ alkyl radical of branched or straight chained or cyclic configuration, or phenyl, or substituted phenyl bearing from 1 to 3 substituents chosen independently from the group consisting of hydrogen, $C_1$–$C_4$ alkyl, $C_1$–$C_4$ alkoxy, halogen, —NHC(O)CH$_3$, amino, or hydroxy;

Z is from 1 to 3 substituents chosen independently from the group consisting of hydrogen, $C_1$–$C_4$ alkyl, $C_1$–$C_4$ alkoxy, or halogen;

Y is from 1 to 3 substituents chosen independently from the group consisting of hydrogen, $C_1$–$C_4$ alkyl, $C_1$–$C_4$ alkoxy, or halogen.

2. A compound according to claim 1 wherein R is phenyl.

3. A compound according to claim 1 wherein R is methyl.

4. The compound according to claim 2 which is 5,7-dichloro-2-benzoyl-4 benzenesulfonylimino-1H-1,4-dihydroquinoline.

5. The compound according to claim 3 which is 5,7-dichloro-2-acetyl-4 benzenesulfonylimino-1H-1,4-dihydroquinoline.

6. The method of inhibiting IL-1 action in a patient in need thereof comprising administering to the patient an IL-1 inhibiting amount of a compound according to claim 1.

7. A pharmaceutical compostion comprising a therapeutically effective amount of a compound according to claim 1 in admixture with a physiologically acceptable carrier.

* * * * *

UNITED STATES PATENT AND TRADEMARK OFFICE
CERTIFICATE OF CORRECTION

PATENT NO. : 5,684,017

DATED : November 4, 1997

INVENTOR(s) : Harrison, et al.

It is certified that error appears in the above-identified patent and that said Letters Patent is hereby corrected as shown below:

At column 10, line 22, the patent reads "Scheme Br" and should read --Scheme B,--.

At column 11, line 48, the patent reads "desiPed" and should read --desired--.

At column 18, line 1, the patent reads "Sandlet" and should read --Sandler--.

Signed and Sealed this

Fifteenth Day of December, 1998

Attest:

BRUCE LEHMAN

*Attesting Officer*  *Commissioner of Patents and Trademarks*